United States Patent
Block et al.

(10) Patent No.: US 10,180,436 B2
(45) Date of Patent: *Jan. 15, 2019

(54) DIAGNOSIS OF LIVER PATHOLOGY THROUGH ASSESSMENT OF ANTI-GAL IGG GLYCOSYLATION

(71) Applicant: Drexel University, Philadelphia, PA (US)

(72) Inventors: Timothy M. Block, Doylestown, PA (US); Mary Ann Comunale, Bangor, PA (US); Anand Mehta, Lansdale, PA (US)

(73) Assignee: Drexel University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/797,666

(22) Filed: Jul. 13, 2015

(65) Prior Publication Data

US 2016/0077106 A1    Mar. 17, 2016

Related U.S. Application Data

(63) Continuation of application No. 12/062,715, filed on Apr. 4, 2008, now Pat. No. 9,110,078.

(51) Int. Cl.
| | | |
|---|---|---|
| *G01N 33/68* | (2006.01) | |
| *G01N 33/574* | (2006.01) | |
| *G06F 19/24* | (2011.01) | |

(52) U.S. Cl.
CPC ... *G01N 33/6854* (2013.01); *G01N 33/57438* (2013.01); *G01N 33/6842* (2013.01); *G01N 2800/085* (2013.01); *G06F 19/24* (2013.01)

(58) Field of Classification Search
CPC .................................................. G01N 33/6854
See application file for complete search history.

(56) References Cited

U.S. PATENT DOCUMENTS

| | | | |
|---|---|---|---|
| 4,786,592 A | 11/1988 | Deal et al. | |
| 5,338,689 A | 8/1994 | Yves et al. | |
| 5,605,807 A | 2/1997 | Dennis | |
| 6,830,895 B2 | 12/2004 | Andrews et al. | |
| 7,335,512 B2 | 2/2008 | Callewaert et al. | |
| 7,776,550 B2 | 8/2010 | Block et al. | |
| 8,183,000 B2 | 5/2012 | Block et al. | |
| 2007/0037221 A1 | 2/2007 | Block et al. | |
| 2009/0166224 A1 | 7/2009 | Yang et al. | |
| 2009/0208926 A1 | 8/2009 | Block et al. | |
| 2009/0253180 A1 | 10/2009 | Block et al. | |

FOREIGN PATENT DOCUMENTS

| | | |
|---|---|---|
| JP | 2002-502037 | 1/2002 |
| WO | WO 01/35105 A1 | 5/2001 |
| WO | WO 2006/078725 A1 | 7/2006 |
| WO | WO 2006/121892 | 11/2006 |

OTHER PUBLICATIONS

Amano, et al., "Production of functional lectin in pichia pastoris directed by cloned cDNA from aleuria aurantia," Biosci. Biotechnol. Biochem., 2003, 67(10), 2277-2279.
Aoki, et al., "Species-Specific Beta-N-acetylgalactosaminylation of Serum IgG Proteins", Biochemica et Biophysica Acta, Mar. 15, 1997, 1334(2-3), 207-213.
Block, et al., "Molecular viral oncology of hepatocellular carcinoma," Oncogene, 2003, 22, 5093-5107.
Block, et al., "Use of targeted glycoproteomics to identify serum glycoproteins that correlate with liver cancer in woodchucks and humans," Proceedings of the National Academy of Sciences of USA, National Academy of Science, Washington, D.C., 2005, 102(3), 779-784.
Bouyain, et al., "An endogenous *Drosophila* receptor for glycans bearing α1,3-linked core fucose residues," J. Biol. Chem., 2002, 277, 22566-22572.
Brechot, "Hepatitis B and C viruses and primary liver cancer," Baillieres Clin. Gastroenterol., 1996, 10(2), 335-373.
Brinkman-van der Linden, et al, Inflammation-Induced Expression of Sialyl Lewis is Not Restricted to a-acid Glycoprotein but also Occurs to a Lesser Extent on a-Antichymotrysin and Haptoglobin, Glycoconjugate Journal, 1998, vol. 15, 177-182.
Buamah, et al. "Serum alpha fetoprotein heterogeneity as a means of differentiating between primary hepatocellular carcinoma and hepatic secondaries," Clin. Chim. Acta, 1984, 139, 313-316.
Callewaert, et al., "Noninvasive Diagnosis of Liver Cirrhosis Using DNA Sequencer-Based Total Serum Protein Glycomics", Nature Medicine, Apr. 2004, 10(4), 429-434.
Chambers, et al, "Abnormally fucosylated haptoglobin as a marker for alcoholic liver disease but not excessive alcohol consumption or non-alcoholic liver disease", Ciinica Chimica Acta, Oct. 1993, 219,177-182.
Comunale, et al., "Comparative proteomic analysis of de-N-glycosylated serum from hepatitis B carriers reveals polypeptides that correlate with disease status", 2004 Proteomics 4, 826-38.

(Continued)

*Primary Examiner* — Taeyoon Kim
*Assistant Examiner* — Tiffany Gough
(74) *Attorney, Agent, or Firm* — Baker & Hostetler LLP

(57) ABSTRACT

Methods for diagnosing pathology of the liver in subject suspected of having such pathology by measuring the glycosylation of anti-gal IgG in various biological fluids of the subject.

17 Claims, 15 Drawing Sheets

Specification includes a Sequence Listing.

(56) References Cited

OTHER PUBLICATIONS

Comunale, et al., "Proteomic Analysis of Serum Associated Fucosylated Glycoproteins in the Development of Primary Hepatocellular Carcinoma", 2006, J Proteome Research. 6, 308-315.
Comunale, et al., "Identification and Development of Fucosylated Glycoproteins as Biomarkers of Primary Hepatocellular Carcinoma," Journal of Proteome Research, Feb. 2009, 8(2), 595-602.
Drake, et al., "Lectin Capture Strategies Combined with Mass Spectrometry for the Discovery of Serum Glycoprotein Biomarkers", 2006, Mol Cell Proteomics 5, 1957-1967.
Drickamer, "C-type lectin-like domains," Curr. Opin. Struct. Biol., 1999, 9, 585-590.
Du, et al., "Differential binding of serum glycoproteins to lectins during hepatic regeneration in hepatocellular carcinoma and fulminant hepatic failure", Clinical Science, Jun. 1990, 78(6), 551-555.
El-Serag, et al., "Trends in survival of patients with hepatocellular carcinoma between 1977 and 1996 in the United States", Hepatology, 2001, 62-65.
Galili, et al., "One Percent of Human Circulating B Lymphocytes Are Capable of Producing the Natural Anti-Gal Antibody", 1993, Blood 82, 2485-93.
Gravel, et al, "Identification of Glycoproteins on Nitrocellulose Membranes Using Lectin Blotting", The Protein Protocols Handbook, 1996, Chapter 97, 603-617.
Guile, et al., "A Rapid High-Resolution High-Performance Liquid Chromatographic Method for Separating Glycan Mixtures and analyzing Oligosaccharide Profiles", Anal Biochem, 1996, 240, 210-26.
Guile, et al., "Identification of highly fucosylated N-linked oligosaccharides from the human parotid gland", Eur J Biochem, 1998, 258, 623-56.
Guo, et al., "Repeated Immunization Induces the Increase in Fucose Content on Antigen-Specific IgG N-Linked Oligosaccharides", Clinical Biochemistry, vol. 38, Feb. 2005, 149-153.
Harlow et al. (Eds.),"Antibodies a Laboratory Manual" Cold Spring Harbor Laboratory; Cold Spring Harbor, NY, 1988, Chapter 6, 139-243.
Hoofnagle, et al. "The treatment of chronic viral hepatitis," N. Engl. J. Med., 1997, 336(5), 47-56.
Ikeda, et al. "A multivariate analysis of risk factors for hepatocellular carcinogenesis: a prospective observation of 795 patients with viral and alcoholic cirrhosis," Hepatology 18, 1993, 47-53.
Ishak, et al., "Histological grading and staging of chronic hepatitis," J. Hepatol, 1995, 22, 696-699.
Ishida, et al. "Molecular cloning and overexpression of flea gene encoding a fucose-specific lectin of aspergillus oryzae," Biosci. Biotechnol. Biochem., 2002, 66(5), 1002-1008.
Iskratsch, et al, "Specificity Analysis of Lectins and Anibodies Using Remodeled Glycoproteins", Analytical Biochemistry, 2009, vol. 386, 133-146.
Kaneko, et al., "Anti-Inflammatory Activity of Immunoglobulin G Resulting from Fc Sialylation", Science, 2006, 313, 670-3.
Kinoshita, et al., "α-Fetoprotein antibody-lectin enzyme immunoassay to characterize sugar chains for the study of liver diseases," Clinica Acta, 1989, 179, 143-152.
Köhler, et al., "Continuous cultures of fused cells secreting antibody of predefined specificity", Nature, 1975, 256, 495-497.
Kweon, et al., "Decreasing fibrogenesis: an immunohistochemical study of paired liver biopsies following lamivudine therapy for chronic hepatitis B", B. J Hepatol, 2001, 35, 749-55.
Lastra, et al., "Changes in the Galactose Content of IgG during Humoral Immune Responses", Autoimmunity, 1998, 28, 25-30.
Lee et al., "The Influence of Glycosylation on Secretion, Stability, and Immunogenicity of Recombinanat HBV Pre-S Antigen Synthesized in *Saccharomyces cerevisiae*", Biochemical and Biophysical Research Communications, Apr. 4, 2003, 303(2), 427-432.
Liljeblad, et al., "A lectin immunosensor technique for determination of alpha1-acid glycoprotine fucosylation", Analytical Biochemistry, 2001, 288(2), 216-224.
Loris, et al., "Structural basis of carbohydrate recognition by the lectin LecB from pseudomonas aeruginosa", J. Mol. Biol., 2003, 331, 861-870.
Mansour, et al., "Distinct binding patterns of fucose-specific lectins from Biomphalaria alexandrine and lotus tetragonolobus to murine lymphocyte subsets", Immunobiology, 2005, 210, 335-348.
Marrero, et al., "GP73, a resident golgi glycoprotein, is a novel serum marker for hepatocellular carcinoma", J. Hepatol. 2005, 43, 1007-1012.
Matsumara, et al, "Glycobiology and Extracellular Matrices: Carbohydrate Binding Specificity of a Fucose-Specific Lectin from Aspergillus Oryzae a Novel Probe for Core Fucose", Journal of Biological Chemistry, Mar. 23, 2007, vol. 282, 15700-15708.
Matsumoto et al., "Alteration of Asparagine-Linked Glycosylation in Serum Transferrin of Patients With Hepatocellular Carcinoma", Clin. Chim. Acta., Jan. 14, 1994, 224(1),1-8.
Mehta, et al., "Increased Levels of Galactose-Deficient Anti-Gal Immunoglobulin G in the Sera of Hepatitis C Virus-Infected Individuals with Fibrosis and Cirrhosis", J. Virology, 2008, 82, 1259-1270.
Miyamoto, et al, "Lectin Histochemistry in Rat Liver Fibrosis Induced by Heterologous Serum Sensitization", J. Vet Med. Sci., Apr. 25, 1997, 681-687.
Miyoshi, et al., "The alpha1-6-fucosyltransferase gene and its biological significance", Biochimica Et Biophysica Acta, Amsterdam, NL, 1999, 1473(1), 9-20.
Naitoh, et al., "Highly enhanced fucosylation of serum glycoproteins in patients with hepatocellular carcinoma", J. Gastroenterol. Hepatol., 1999, 14, 436-445.
Nascimento, et al., "Algal Lectin Binding to Core (a1-6) Fucosylated N-glycans:Structural Basis for Specificity and Production of Recombinant Protein", Glycobiology Advance Access, Jan. 30, 2015, 1-10.
Nguyen, et al., "Racial differences in effectiveness of α-fetoprotein for diagnosis of hepatocellular carcinoma in hepatitis C virus cirrhosis", Hepatology, 2002, 36, 410-417.
Nimmerjahn, et al., "Agalactosylated IgG antibodies depend on cellular Fc receptors for in vivo activity", 2007 Proc Natl Acad Sci, USA 104, 8433-7.
Nydegger, et al., "Solid Organ Transplantation Across Te ABO Histo-Blood Group Barrier: A Case Report", Transplantation Proceeding, Jun. 2004, 35, 1554-1557.
Oka, et al., "Prospective study of α-fetoprotein in cirrhotic patients monitored for development of hepatocellular carcinoma", Hepatology, 1994, 19, 61-7.
Pateron, et al., "Prospective study of screening for hepatocellular carcinoma in Caucasian patients with cirrhosis", J. Hepatol., 1994, 20, 65-71.
Rattan, et al., "Protein Synthesis: Posttranslational Modifications and Aging", Ann. NY Acad. Sci.,1992, 663, 48-62.
Routier, et al. "Quantitation of the Oligosaccharides of Human Serum IgG From Patients With Rheumatoid Arthritis: A Critical Evaluation of Different Methods", Journal. Immunological Methods, Apr. 1998, 213, 113-130.
Roy, et al., "Detection of root mucilage using an anti-fucose antibody," Ann. Botany, 2002, 89, 293-299.
Rudd, et al., "Glycoproteins: Rapid Sequencing Technology for N-linked and GPI Anchor Glycans", 1999 Biotechnol Genet Eng Rev, 16-21.
Rudd, et al., "Rapid, sensitive sequencing of oligosaccharides from glycoproteins", 1997, Curr Opin Biotechnol 8, 488-97.
Ryden, et al, "Diagnostic Accuracy of Alpha(1)-acid Glycoprotein Fucosylation for Liver Cirrhosis in Patients Undergoing Hepatic Biopsy", Clinical Chemistry, Dec. 2002, 48(12), 2195-2201.
Ryden, et al., "Lectin ELISA for Analysis of a1-Acid Glycoprotein Fucosylation in the Acute Phase Response", Clin. Chem., 1999, 45(11), 2010-2012.
Schmitt, et al. "Structure of Pre-S2 N- and O-linked Glycans in Surface Proteins From Different Genotypes of Hepatitis B Virus", J. Gene, Viral, Jul. 2004, 85, 2045-2053.
Seifter, et al, "Analysis for Protein Modifications and Nonprotein Cofactors", Methods Enzymol., 1990, 182, 626-646.
Srikrishna, et al., "Fucoseβ-1-ser is a new type of glycosylation: using antibodies to identify a novel structure in *Dictyostelium*

(56) References Cited

OTHER PUBLICATIONS

*discoideum* and study multiple types of fucosylation during growth and development", Glycobiology, 1998, 8, 799-811.
Steel, et al, "A Proteomic Approach for the Discovery of Early Detection Markers of Hepatocellular Carcinoma", Disease Markers, 2001, 17(3), 179-189, epublished online Jun. 7, 2002.
Thompson, Abnormally-fucosylated haptoglobin: a cancer marker for tumour burden but not gross liver metastasis, Br. J. Cancer, 1991, 64, 386-390.
Tockman, et al., "Considerations in Bringing a Cancer Biomarker to Clinical Application", Cancer Res., 1992, 52, 2711s-2718s.
Um, et al., "α-Fetoprotein Impairs APC Function and Induces Their Apoptosis", J. Immunol., Aug. 1, 2004, 173 , 1772-1778.
Wang, et al., "Novel Fucosylated Biomarkers for the Early Detection of Hepatocellular Carcinoma", Cancer Epidemiol. Biomarkers & Prevention, Jun. 2009, 18(6), 1914-1921.
Wang, et al., "Utility of Lentil Lectin Affinity of A-Fetoprotein in the Diagnosis of Hepatocellular Carcinoma", J. Hepatology, Aug. 1996, 25(2), 166-171.
Weinberg, et al., "A Tetramethylbenzidine/Tungstate Reaction for Horseradish Peroxidase Histochemistry", The Journal of Histovchemisty and Cytochemistry, Aug. 1991, 39(8), 1143-1148.
Yamamoto, et al., "Lens Culinaris Agglutinin-Reactive α-Fetoprotein, an alternative variant to α-Fetoprotein in Prenatal Screening for Down's Syndrome", Human Reproduction, Nov. 2001, 16(11), 2438-2444.
Zoli, et al., "Efficacy of a surveillance program for early detection of hepatocellular carcinoma," Cancer, 1996, 78, 977-983.

EEQYNSTYR    SEQ ID NO:1

EVQLVESGGGLVKPGGSLR    SEQ ID NO:2

NTLYLQMNSLK    SEQ ID NO:3

| M.W Expected | M.W Observed | Sequence | Accession# | Identity |
|---|---|---|---|---|
| 1189.51 | 1190.54 | EEQYNSTYR<br>SEQ ID NO:1 | AAA02914 | IgG Heavy Chain |
| 1882.04 | 1882.06 | EVQLVESGGGLVKPGGSLR<br>SEQ ID NO:2 | 2119327A | anti-alpha-galactosyl epitope antibody |
| 1324.69 | 1325.57 | NTLYLQMNSLK<br>SEQ ID NO:3 | 2119327A | anti-alpha-galactosyl epitope antibody |

FIGURE 2C

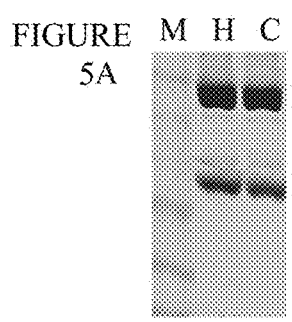
FIGURE 5A
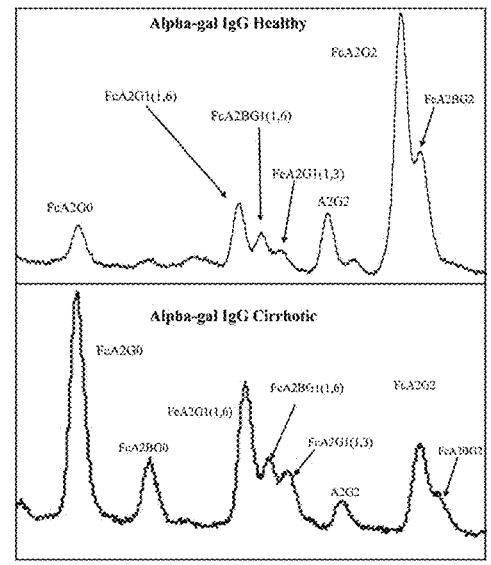
FIGURE 5B
FIGURE 5C

DIAGNOSIS OF LIVER PATHOLOGY THROUGH ASSESSMENT OF ANTI-GAL IGG GLYCOSYLATION

CROSS-REFERENCE TO RELATED APPLICATIONS

This application is a continuation of U.S. Ser. No. 12/062,715, filed Apr. 4, 2008 (now allowed), the entire contents of which are incorporated herein by reference.

GOVERNMENT SUPPORT

This invention was made with government support under Contract Nos. R01 CA120206-01 and U01 CA84951 awarded by the National Cancer Institute. The government has certain rights in the invention.

SEQUENCE LISTING

The instant application contains a Sequence Listing which has been submitted electronically in ASCII format and is hereby incorporated by reference in its entirety. Said ASCII copy, created on May 25, 2017, is named 101915_000579_SL.TXT and is 842 bytes in size.

FIELD OF THE INVENTION

The invention relates generally to the field of immunodiagnostics for detecting alterations in the glycosylation of the immunoglobulin that is reactive towards the alpha-gal epitope, which is a marker for liver diseases such as hepatocellular carcinoma, hepatitis, and cirrhosis.

BACKGROUND OF THE INVENTION

In this application we disclose a specific aspect of the invention disclosed in U.S. patent application Ser. No. 11/418,598, filed May 5, 2006, the contents of which are incorporated by reference. Further, all references cited herein are incorporated herein by reference in their entireties.

SUMMARY OF THE INVENTION

The present invention features a method for diagnosing pathologies of the liver or biliary system by obtaining biological fluid from the subject, quantifiably detecting glycosylation on immunoglobulin reactive for the antig-gal epitope ("anti-gal IgG") in the biological fluid, and comparing the detected glycosylation with reference values for glycosylation of anti-gal IgG in subjects with no liver pathology, with known liver pathologies, or both; said glycosylation relative to the reference values being indicative of the presence or absence of the pathology of the liver, and preferably for liver fibrosis, cirrhosis, or hepatocellular carcinoma. The preferred glycosylation that is a reduction in galactosylation that correlates with an increase association with fucose binding lectins. Suitable biological fluids include whole blood, serum, urine, saliva, tears, or mucous.

The detection of glycosylated anti-gal IgG can proceed via any assay suitable in the art. The detection reagent can directly label the glycosyl moieties, for example, via carbohydrate specific chemicals or dyes, or via labeled lectins, labeled carbohydrate binding proteins, or labeled antibodies. The detection reagent can be a secondary reagent, for example, by first capturing anti-gal IgG and then contacting the capture reagent-anti-gal IgG complex with a labeled secondary reagent. Detection can proceed by separating glycosyl moieties from anti-gal IgG prior to the quantifiable detection of glycosylation. Detection can proceed by separating glycosylated anti-gal IgG from the test sample prior to the quantifiable detection of glycosylation.

BRIEF DESCRIPTION OF THE DRAWINGS

FIG. 2A is a photograph of a one dimensional electrophoretic gel of the major fucosylated proteins in the serum of cirrhotic patients were identified by extracting fucosylated proteins from serum using fucose specific lectins. In lane 1 are the lectin reactive proteins from healthy individuals; in lane 2 are the lectin reactive proteins from cirrhotic individuals. The 50 kd species, which is altered in the two patient groups is indicated with the asterisks. FIG. 2B are LC MS/MS graphs of the 50 kd species was digested with trypsin and the protein identified via LC MS/MS analysis. The $MS^2$ spectra for the three major peptides identified are shown (SEQ ID NOS 1-3, respectively, in order of appearance). FIG. 2C is a chart describing the major identified fucosylated proteins (SEQ ID NOS 1-3, respectively, in order of appearance) observed in cirrhotic samples corresponded to IgG reactive towards the alpha-gal epitope.

FIGS. 5A-C are respectively a photograph and HPLC graphs of glycan sequencing of anti-gal IgG from healthy or cirrhotic individuals. FIG. 5A is a photograph of a one dimensional electrophorectic gel after Coomassie staining of anti-gal IgG purified from either healthy individuals (H) or cirrhotic individuals (C). The Marker lane is also indicated (M). The heavy (H) and light chains (L) are indicated. FIG. 5B-C is an HPLC graph depicting the glycan analysis of the desialylated N-linked glycans associated with the heavy chain from healthy individuals (FIG. 5B) or a cirrhotic individual (FIG. 5C). For structures presented in panels B-C: FcA2G0, core fucosylated (1,6) agalactosylated biantennary glycan; FcA2BG0, core fucosylated (1,6) agalactosylated biantennary glycan with a bisecting N-acetylglucosomine (GlcNac); FcA2G1 (1,6) core fucosylated (1,6) biantennary glycan with a single galatose residue on the 1,6 arm; FcA2BG1 (1,6) core fucosylated (1,6) biantennary glycan with a single galatose residue on the 1,6 arm and a bisecting GlcNac; FcA2G2G1 (1,3), core fucosylated (1,6) biantennary glycan with a single galatose residue on the 1,3 arm; FcA2G2, core fucosylated biantennary N-glycan (FcA2G2); FcA2BG2, bisected core fucosylated biantennary N-glycan.

FIG. 6A is a photograph of the detection of FcA2G0 glycan structure in IgG from healthy individuals (purchased from Sigma Chemicals) was digested overnight with Sialidase (*Arthrobacter ureafaciens*) and beta(1-4)-Galactosidase (Jack Bean) to create IgG molecules with the degalactosylated glycans observed in patients with cirrhosis. As a control, a mock sample treated identically, but without enzyme, was used. While IgG purified from healthy individuals has low reactivity with the fucose binding lectin, IgG purified from either cirrhotic individuals or IgG from healthy serum that has been treated with the sialidase and beta galactosidase has much greater reactivity, indicating that the lectin reactivity is directly associated with the FcA2G0 glycan structure. FIG. 6B contains two HPLC graphs depicting the glycan analysis of IgG from either mock treated samples (top) or enzyme treated samples (bottom) to confirm enzymatic digestion. The major peaks are indicated, and structures comprise A2G2S1, mono-sialylated biantennary glycan; FCA2G2S1, mono-sialylated core fucosylated biantennary N-glycan; FCA2BG2S1, mono-sialylated core fucosylated biantennary glycan with a bisecting GlcNac; A2G2S2, disialyated biantennary glycan; FCA2BG2S2, disialyated core fucosylated biantennary glycan; FcA2BG2S2, disialyated core fucosylated biantennary glycan with a bisecting GlcNac. FIG. 6C is a graph quantifying the results shown in FIG. 6B. X-axis is the glycan structure as detailed in panel B, Y-axis is the relative contribution of each glycan structure in the total N-linked glycan profile.

FIG. 7A is a scatter-plot of control individuals, individuals with HCV induced cirrhosis and individuals with HCV induced cirrhosis plus HCC. The n value, mean and standard error, are provided for each group below the graph. X-axis represents the patient group. Y-axis is fold increase in lectin reactive IgG as compared to commercially purchased sera. Statistical difference was obtained between the HCV induced cirrhosis group and control subjects (P<0.0001, Mann-Whitney test). FIG. 7B is a graph depicting the level of lectin reactive anti-gal IgG was measured in patients with HBV, autoimmune, alcohol or cryptogenic induced cirrhosis. The n value, mean, and standard error are provided for each group below the graph. X-axis represents the patient group. Y-axis is fold increase in fucosylated IgG as compared to commercially purchased sera. Values for each group are provided as mean and standard error of the mean. Statistical difference was obtained for all cirrhosis groups and control subjects (p<0.0001, Mann-Whitney test) but not between individual cirrhotic groups.

FIG. 8A is a graph depicting the level of lectin reactive anti-gal IgG in the control group, people with stage 1-2 fibrosis, stage 3-5 fibrosis and cirrhosis. The mean value for each group is plotted along with the 95% confidence interval for the mean. For graph, X-axis represents the patient group. Y-axis is fold increase in lectin reactive IgG as compared to commercially purchased serum. The n value, mean, and standard error are provided for each group below the graph. In this figure, all patients with cirrhosis (from FIGS. 5A & 5B) are included. FIG. 8B is a graph depicting the ROC analysis comparing people with Stage 1&2 fibrosis with control group. Using an optimal cutoff of 3 fold above commercially purchased sera, fucosylated immunoglobulin has a sensitivity of 84% and a specificity of 87%. FIG. 8C is a graph depicting the ROC analysis comparing Stage 1-2 fibrosis with 3-6 fibrosis/cirrhosis. Using an optimal cutoff of 5 fold above commercially purchased sera, fucosylated immunoglobulin has a sensitivity of 91% and a specificity of 79%.

DETAILED DESCRIPTION OF ILLUSTRATIVE EMBODIMENTS

Figure 1:
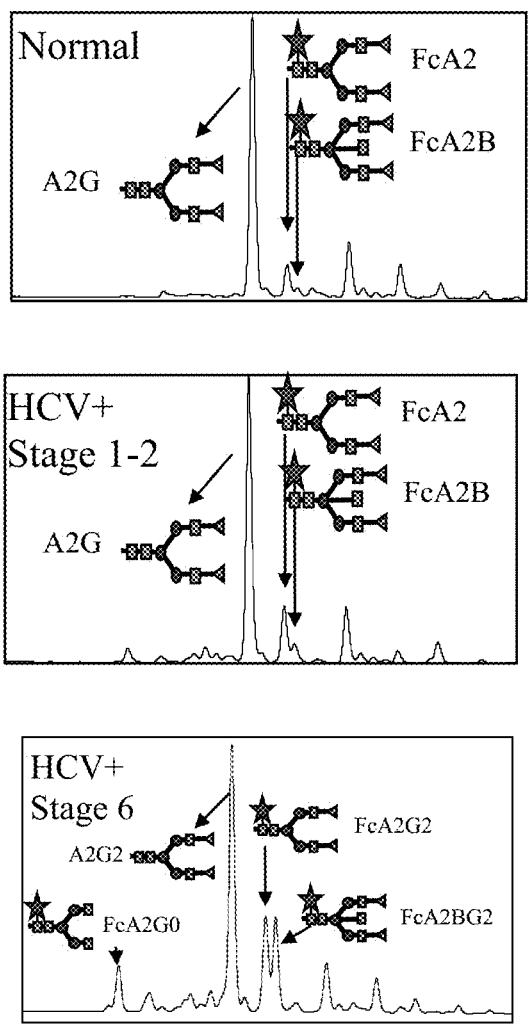
FIG. 1 are a series of HPLC graphs showing total serum desialyated glycan profiles from control samples (top), HCV samples with stage 1&2 fibrosis (middle) or HCV patients with biopsy confirmed cirrhotic (stage 5-6) samples (bottom). The major peaks of interest are indicated and include a simple biantennary glycan (A2G2), a core fucosylated biantennary glycan (FcA2G2) and a core fucosylated bisected biantennary glycan (FcA2BG2). Cirrhotic samples were from patients with stage 6 fibrosis. Squares represent N-acetylglucosamine monosaccharides (GlcNAc); circles represent mannose; triangles represent galactose and the star represents the fucose.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations may be used in the specification and examples: HBV, hepatitis B virus; HCV, hepatitis C virus; AFP, alpha-fetoprotein; HCC, hepatocellular carcinoma; HPLC, high performance liquid chromatography; Fc, fucosylated.

As used in this specification and the appended claims, the singular forms "a", "an" and "the" include plural referents unless the content clearly dictates otherwise. Thus, for example, reference to "a cell" includes a combination of two or more cells, and the like.

"Anti-gal IgG" refers to the immunoglobulins of the G class that recognize a specific sugar linkage on glycolipids and glycoproteins, that is present in non-human antigens. This sugar linkage (Gal α-1-3Galβ1-(3)4GlcNAc-R), referred to as the alpha-gal epitope, is absent in humans but is abundantly synthesized by bacteria and nonprimate mammals. Anti-gal antibodies are naturally occurring antibodies that, in healthy subjects, constitute ~1% of total serum IgG.

The following examples are provided to describe the invention in more detail. They are intended to illustrate, not to limit the invention.

Example 1: General Experimental Procedures

Patients:
Patients for the analysis were obtained from the University of Michigan under a study protocol that was approved by the University of Michigan's Institutional Review Board. In addition, written informed consent was obtained from each subject. Demographic and clinical information was obtained, and a blood sample was collected from each subject. The blood sample from patients with chronic HCV infection was obtained at the time of liver biopsy and antiviral therapy. HCV was defined as the presence of HCV RNA with a lower limit of detection of <50 IU/mL at the University of Michigan Clinical Laboratory. All liver biopsies were at least 30 mm long and 1.4 mm wide and graded by three hepatic pathologists in a blinded fashion and the amount of fibrosis was graded using the Ishak scoring system. (Ishak, et al., 1995. J Hepatol 22:696-9). Details on all patients are provided in Table 1.

fibrosis, and 10 patients with cirrhosis to determine the glycan changes that occur with the development of liver cirrhosis. Briefly, 5 µl of serum was absorbed into a dehydrated 12% tris-glycine gel plug. The gel plug was reduced and alkylated and the proteins fixed using 10% methanol and 7% acetic acid. The N-linked glycans were removed using N-Glycanase Plus (Prozyme, San Leandro, Calif. USA) as done previously (Block, et al., 2005. Proc Natl Acad Sci

TABLE 1

Description of control subjects and patients with liver disease.

| | | Stage of Disease (Ishak)[1] | | | | |
|---|---|---|---|---|---|---|
| Variables | Controls | 1-2 | 3-5 | 6 (complete cirrhosis) | Non-HCV Cirrhosis | HCC + Cirrhosis |
| Sample Size | 113 | 24 | 19 | 57 | 34 | 87 |
| Age[2] | 51 ± 11 | 50 ± 6 | 51 ± 4 | 53 ± 8 | 55 ± 8 | 56 ± 7 |
| % NHW/AA/H/Asian[3] | 90/10/0/0 | 98/1/1/0 | 96/2/1/1 | 85/11/2/2 | 98/0/1/0 | 88/4/2/6 |
| ALT (IU/mL)[4] | 28 ± 5 | 75 ± 7 | 71 ± 11 | 79 ± 19 | 85 ± 26 | 75 ± 12 |
| AST (IU/mL)[5] | 26 ± 3 | 73 ± 5 | 69 ± 8 | 93 ± 11 | 108 ± 24 | 101 ± 18 |
| Total Bilirubin[6] (mg/dL) | 0.3 ± 0.1 | 0.3 ± 0.2 | 0.3 ± 0.4 | 1.2 ± 1.3 | 1.4 ± 0.7 | 1.6 ± 1.3 |
| % HCV Genotype 1[7] | NA | 78 | 72 | 76 | NA | 75 |
| HCV Viral load[8] (copies/mL) | 0 | 1.3 ± .8 | 1.6 ± 1 | 1.7 ± 1.5 | NA | 1.4 ± 1.3 |
| serum gamma-globulin (g/dL)[9] | 0.54 ± 0.1 | 0.85 ± 0.2 | 1.1 ± 0.4 | 1.3 ± 0.8 | 1.4 ± 0.8 | 1.1 ± 0.3 |

[1]Fibrosis staging based upon ISHAK scoring system. For this study, stage 5 or greater is considered cirrhotic.
[2]Mean age in years.
[3]NHW = non-Hispanic White; AA = African American; H = Hispanic;
[4]ALT = alanine aminotransferase;
[5]AST = aspartate aminotransferase.
[6]P = 0.02 HCC vs. controls, fibrosis stage 1 and 2; otherwise no differences.
[7]HCV = hepatitis C. Non-HCV cirrhosis = 5 hepatitis B, 6 autoimmune hepatitis, 14 cryptogenic cirrhosis, and 9 alcoholic. NA = not applicable.
[3,7,8]No significant differences among groups
[4,5,9]p < 0.0001 Fibrosis stage 1-6 and HCC vs. controls A group of individuals with no history of liver disease, alcohol consumption less than 40 gm a week, and no risk factors for viral hepatitis were enrolled from the General Internal Medicine clinics. All subjects in this control group were documented to have normal liver biochemistry and negative HCV antibodies. Patients with HCV induced cirrhosis plus HCC, were enrolled from the Liver Clinic during this period. The diagnosis of HCC was made by histopathology (n=87, including all T1 lesions), and if histopathology was not available by two imaging modalities (dynamic ultrasound [US], magnetic resonance imaging [MRI], or computed tomography). All patients with HCC were determined to have underlying cirrhosis based on histopathology (85%) and by clinical parameters (15%). Each of the patients with a histological diagnosis of cirrhosis had a normal US and, if serum AFP was elevated, a MRI of the liver within 3 months prior to enrollment and another one 6 months after enrollment that showed no liver mass, in order to confirm that they have not developed HCC. The cirrhotic controls have been followed for a median of 12 months (range 7-18 months) after enrollment, and no one has developed HCC. The etiology of the liver disease for the patients without HCV infection was determined as previously described (Marrero et al., 2005. J. Hepatology 43:1007-12) and the definition of cirrhosis in these patients was also determined by histology.

Glycan Analysis of Total Serum.

Total serum glycan analysis was performed on composite samples from 10 healthy patients, 10 patients with mild USA 102:779-84; Comunale, et al., 2006 J Proteome Research. 6:308-315; Comunale, et al., 2004 Proteomics 4:826-38) and labeled with 2-aminobenzoic acid (Ludger LTD, Abingdon, UK) according to the manufacture's directions (Guile, et al., 1996. Anal Biochem 240:210-26; Rudd, et al., 1999 Biotechnol Genet Eng Rev 16:1-21). Desialation of labeled N-glycan was performed via incubation of dried glycan with 1 µnit/ML of Arthrobacter ureafaciens sialidase (Prozyme), as per manufacturer's directions. Glycan structures were identified by the calculation of GU value, through comparison to known standards and by sequential exoglycosidase digestion as before (Guile, et al., 1998. Eur J Biochem 258:623-56; Guile, et al., 1996. Anal Biochem 240:210-26).

Proteomic Identification of Fucosylated Glycoproteins:

To determine the identity of those proteins that contained core fucosylated glycans, we utilized specific sugar (glycan) binding proteins (lectins) to enrich for fucosylated proteins prior to proteomic analysis via mass spectrometry. Briefly, lectin extraction was performed using agarose bound *Aleuria Aurantia* Lectin (AAL) (Vector Laboratories, Ventura, Calif.) and Affi Sep-AAL Absorption Buffer and Elution Buffers (GALAB, Germany) Fucosylated proteins from 10 healthy individuals and 10 cirrhotic individual (serum was combined) were extracted and the fucosylated proteins dissolved in loading buffer and resolved by electrophoresis through 12% SDS/polyacrylamide gels (SDS/PAGE). Proteins of interest were excised from the gel and identified via LC MS/MS. Samples were de-N-glycosylated prior to LC MS/MS analysis. Peptide identification was preformed on a ThermoFinnigan LCQ ion trap mass spectrometer (Thermo-Finnigan, San Jose, Calif.) equipped with on-line microcapillary HPLC (Eldex, Napa, Calif.) and microspray ionization source as done previously (Comunale, et al., 2006. J Proteome Research. 6:308-315). Peptide searches were performed using Sequest (Thermo-Finnigan Corp.) against the Swiss-Prot human database. Xcorr versus change state parameters were set to 1.50, 2.0 and 2.50.

Lectin Fluorophore-Linked Immunosorbent Assay (FLISA):

For the analysis of the glycan modification of total IgG and anti-gal IgG, we utilized a lectin-FLISA based approach. Briefly, to remove the fucosylation of the capture antibody (mouse anti-human IgG, Bethyl Laboratories, Montgomery, Tex.), antibody was incubated with 10 mM sodium periodate for 1 hour at 4° C. An equal volume of ethylene glycol was added and the oxidized antibody brought to a concentration of 10 µg/mL with sodium carbonate buffer, pH 9.5. Antibody (5 µg/well) or human serum albumin attached to Galα1-3Galβ1-3GlcNAc (HSA-alpha-gal; Dextra Labs) or HSA alone (Sigma-Aldrich), was added to the plate and following incubation washed with 0.1% Tween 20/PBS 7.4 and blocked overnight with 3% BSA/PBS. For analysis, 3 µl of serum was diluted in 97 µL pf 3% BSA/PBS and added to the plates for 2 hours and washed 5 times in lectin incubation buffer (10 mM Tris pH 8.0, 0.15M NaCl, 0.1% Tween 20) before fucosylated IgG detected with a biotin conjugated *Aleuria aurantia* (AAL) lectin (Vector Laboratories, Burlingame, Calif.). Bound lectin was detected using IRDye™ 800 Conjugated streptavidin and signal intensity measured using the Odyssey® Infrared Imaging System (LI-COR Biotechnology, Lincoln, Nebr.). In all cases sample intensity was compared to commercially purchased human serum (Sigma Inc., St Louis, Mo.) (Kaneko, et al., 2006 Science 313:670-3; Kweon, et al., 2001 B. J Hepatol 35:749-55). All samples were run in triplicate and inter sample variation was less than 1%.

Purification and Glycan Analysis of Anti-Gal IgG.

For analysis of anti-gal IgG, the same samples described above were utilized. Synthetic Galα1-3Galβ1-3GlcNAc-HSA (Dextra Labs, Reading, United Kingdom) was coupled to a NHS-activated Sepharose 4 Fast Flow affinity column (GE Healthcare, Piscataway, N.J.) as per manufacturer's directions. Briefly, 50 µl of serum was incubated with the column and the column washed with five column volumes of TBS-T (Tris buffered saline with 0.1% Tween-20), followed by one column volume was with TBS. The Galα1-3Galβ1-3GlcNAc specific IgG was eluted using 0.1M NaCl$_2$/0.1M Glycine pH 2.8 and immediately neutralized. For this study, an equal amount of anti-gal IgG (1 µg) was reduced, alkylated and separated on a 12% tris-glycine acrylamide gel and stained using Colloidal Coomassie. Anti-gal IgG bands were excised, destained and glycan analysis preformed as done previously and as described above (Block, et al., 2005 Proc Natl Acad Sci USA 102:779-84; Comunale, et al., 2006 J of Proteome Research. 6:308-315).

Exoglycosidase Treatment of Purified IgG.

IgG was purified from commercially purchased human serum (Sigma Chemicals) using the Melon Gel IgG Purification Kit (Pierce, Rockland, Ill.). Purified IgG was subsequently concentrated and buffered exchanged TBS. Half of the sample was incubated with 5 units/ML *Arthrobacter ureafaciens* sialidase (Prozyme), 5 units/ML Jack Bean beta-galactosidase (Prozyme) and 5× exoglycosidase buffer (0.5 M Citrate Phosphate buffer, pH 4.5, 0.2 mM Zn(O$_2$CCH$_3$)$_2$, 150 mM NaCl$_2$) at 37° C. overnight. The other half of the IgG sample was incubated with buffer alone at 37° C. overnight. The next day, half of the sample was tested for lectin reactivity as described above and the other half was used for HPLC glycan analysis to confirm exoglycosidase digestion.

Statistical Analysis:

Descriptive statistics for stage patients were compared by scatter plots that included the outliers. All values were reported as mean values+/−standard error unless otherwise stated. As the data did not follow typical Gaussian distribution, a non-parametrical test (two-tailed, 95% confidence, Mann-Whitney Test) was used to determine statistical difference between groups. A two-tailed P-value of 0.05 was used to determine statistical significance. All analyses were performed using GraphPad Prism (San Diego, Calif., USA).

Example 2: Alterations in the Human Serum Glycome and Identification of Anti-Gal IgG as the Predominant Altered Glycoprotein in Patients with Cirrhosis FIG. 1 shows the desialylated N-linked glycan analysis of total serum from either control patients (left), HCV patients with stage 1-2 fibrosis (middle) or patients with HCV and biopsy confirmed cirrhosis (right) as performed by normal phase HPLC (Guile, et al., 1996. Anal Biochem 240:210-26; Rudd, et al., 1997 Curr Opin Biotechnol 8:488-97). Each peak corresponds to a different glycan structure and as FIG. 1A shows significant changes in N-linked glycosylation can be seen in patient serum with the development of cirrhosis. Peaks that are significantly altered are indicated and correspond to an agalactosylated core fucosylated biantennary N-glycan (FcA2G0), a core fucosylated biantennary N-glycan (FcA2G2) and a bisected core fucosylated biantennary N-glycan (FcA2BG2).

Figure 2A:
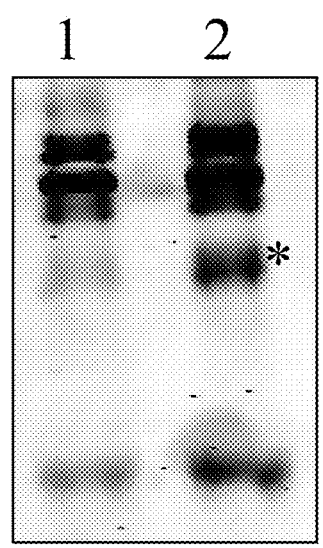
FIGS. 2A-B are respectively a photograph, liquid chromatography graph, and chart identifying the major lectin reactive protein(s) in the serum of patients with fibrosis/cirrhosis.
Figure 2B:
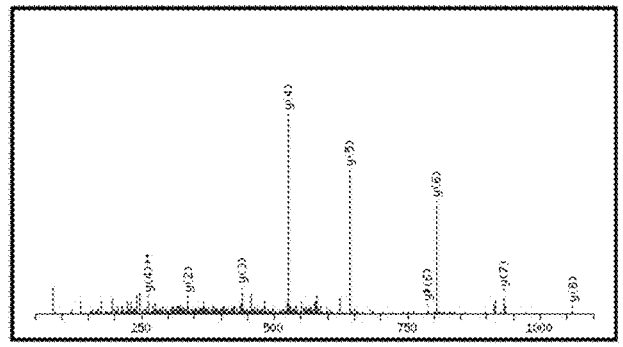
Figure 2B:
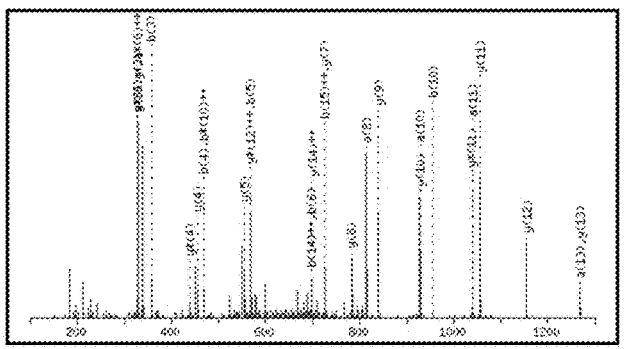
Figure 2B:
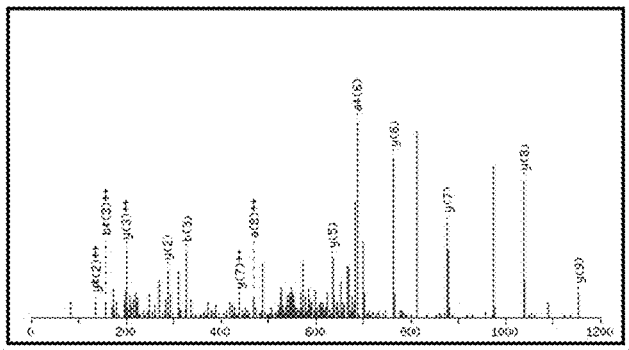

The identity of the major glycoproteins to which the fucosylated glycan were attached was determined by two approaches. The first was the observation that the difference in glycosylation as observed in FIG. 1 was abolished if immunoglobulin was depleted from serum, prior to N linked glycan analysis. Although the serum depletion approach provided circumstantial evidence that immunoglobulins were the source of elevated fucose in the serum, a second method was used to positively identify the fucosylated proteins. Undenatured proteins containing fucosylated N-linked glycans were extracted from serum by passing over columns with the fucose binding lectin, AAL. Polypeptides binding to the lectin represent the serum "fucome" or "fucosylated proteome". In this way, the fucosylated proteome was analyzed by one dimensional gel electrophoresis from healthy individuals or from patients with cirrhosis. As FIG. 2A shows, several difference can be seen between the fucosylated proteome from healthy patients and patients with cirrhosis. A species at 50 kd was highly elevated in patients with cirrhosis and was further examined by trypsination of the protein followed by LC MS/MS analysis for protein identification (FIG. 2B). Three of the peptides identified are shown and were used to identify the 50 kd species as IgG with reactivity to the sugar Gal α-1-3Galβ1-(3)4GlcNAc, commonly referred to as the alpha-gal epitope (FIGS. 2B and 2C).

Figure 3:
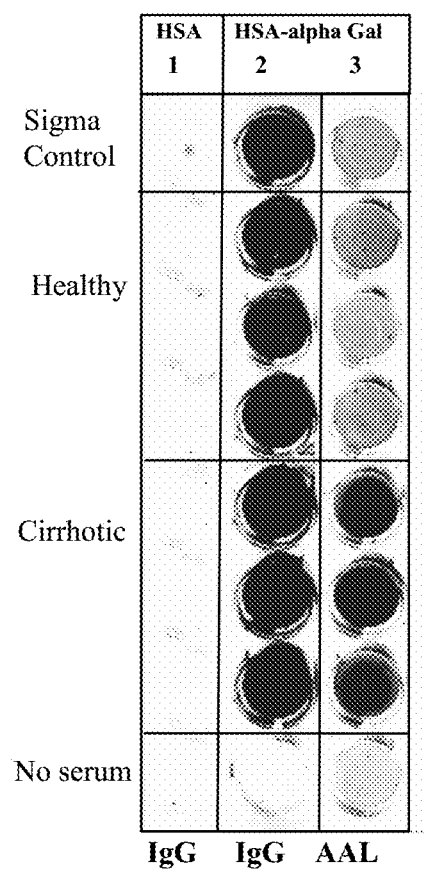
FIG. 3 is a photograph of the detection of altered anti-gal IgG glycosylation in samples from patients with cirrhosis. Either human serum albumin (HSA, column 1) or synthetic Gal α-1-3Galβ1-(3)4GlcNAc linked HSA (columns 2&3) was plated onto 96 well plates and incubated with human serum from four healthy control individuals or from three individuals with cirrhosis. Captured IgG was either detected using anti-human IgG conjugated secondary antibody (columns 1 &2) or using the fucose specific lectin AAL (column 3).

Example 3: Confirmation of Alteration in the Glycosylation of Alpha-Gal Reactive IgG Confirmation of specificity to the alpha-gal epitope was performed through a plate based assay to measure the level of lectin reactive IgG specific for the epitope. As shown in FIG. 3, synthetic alpha-gal linked to human serum albumin (HSA) was plated onto 96 well plates and incubated with human serum from four healthy control individuals, or 3 individuals with cirrhosis. Captured IgG was detected using anti-human IgG conjugated secondary antibody or using the fucose specific lectin AAL. As a control, unconjugated human serum albumin (HSA) was plated on adjacent wells to measure specificity of binding. Columns 1 and 2 of FIG. 3 show the binding of human IgG to wells containing either HSA (column 1) or HSA-alpha-gal (column 2) detected using an anti-human IgG secondary antibody. As this Figure shows, and not surprisingly, while no human IgG molecules bind to the HSA (column 1), strong binding is observed to the HSA conjugated with the alpha-gal sugar (column 2). The binding is present in all serum samples and is consistent with the report of anti-gal antibodies being present in the serum of all patients (Galili, et al., 1993 Blood 82:2485-93). In column 3 is the lectin reactivity of the anti-gal antibody. As column 3 shows, only the captured IgG from patients with cirrhosis were reactive to the lectin, suggesting that the alpha-gal antibody becomes lectin reactive with the development of severe fibrosis or cirrhosis. The relative increase in anti-gal IgG, total IgG, and AAL reactive anti-gal IgG is shown in Table 2.

TABLE 2

The relative levels of total IgG, anti-gal IgG and AAL reactive anti-gal IgG in patients with limited fibrosis, severe fibrosis, or cirrhosis.

| Patient Group[1] | Fold greater than healthy purchased control[2] | | |
|---|---|---|---|
| | Total IgG[3] | Anti-gal IgG[4] | AAL reactive anti-gal IgG[5] |
| Experimental control samples | 1 +/− 0.1 | 1 +/− 0.1 | 1 +/− 0.1 |
| F1-F2 | 1.8 +/− 0.1 | 2 +/− 0.2 | 3 +/− 0.2 |
| F3-F5 | 2.1 +/− 0.2 | 3.5 +/− 0.1 | 9 +/− 0.2 |
| Cirrhotic | 2.4 +/− 0.1 | 3.7 +/− 0.1 | 15 +/− 0.2 |

[1]Fibrosis staging based upon ISHAK scoring system. Samples were combined for analysis. 10 samples per group were used for analysis.
[2]All values are provided as relative fold increases over commercially purchases sera.
[3]The relative increase in IgG as compared to commercially purchased sera. Numbers are fold increase +/− standard deviation.
[4]The relative increase in anti-gal IgG as compared to commercially purchased sera. Numbers are fold increase +/− standard deviation
[5]The relative increase in AAL reactive anti-gal IgG as compared to commercially purchased sera. Numbers are fold increase +/− standard deviation.

Figure 4:
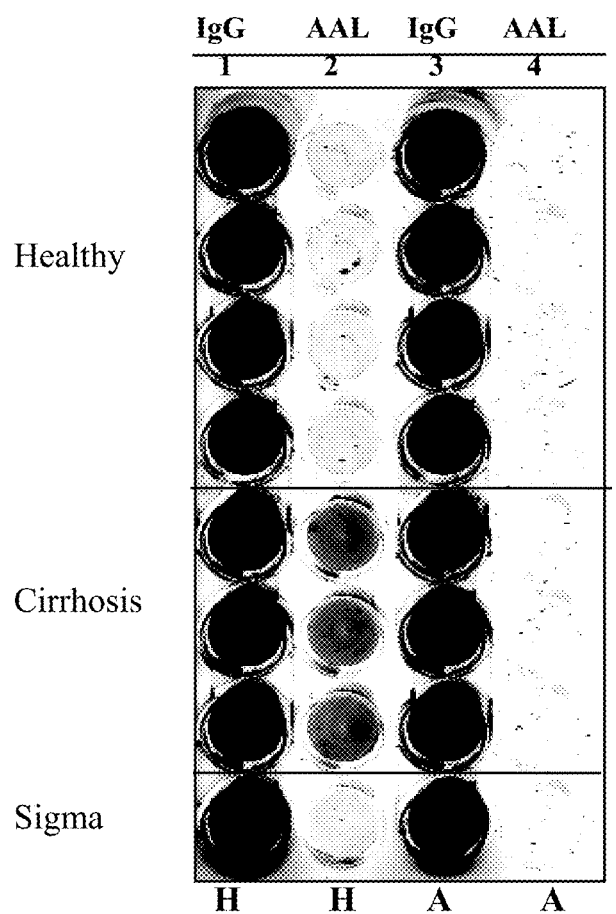
FIG. 4 is a photograph of the detection of altered anti-gal IgG fucosylation in samples from patients with cirrhosis. Removal of heterophilic alpha-gal antibodies prevents lectin reactivity of IgG from cirrhotic patients. IgG from either healthy individuals, or individuals with cirrhosis were captured from serum using a mouse anti-human IgG antibody. The amount of captured IgG (lane 1) or the level of AAL lectin reactivity (lane 2) was determined as in FIG. 3. Samples were either pre-cleared with HSA (lanes 1&2) or with alpha-gal HSA (lanes 3&4 before analysis. (H), pre-cleared with HSA; (A), pre-cleared with alpha-gal HSA.

Example 4: Alpha-Gal Antibodies Become Selectively Reactive to the Fucose Binding Lectin, in People with Fibrosis and Cirrhosis Increased binding of the AAL lectin to IgG from cirrhosis patients could be abolished if samples were pre-cleared of anti-alpha-gal antibodies prior to analysis. FIG. 4 shows the results of a human IgG lectin-FLISA using either sera from four healthy individuals or sera from three patients with cirrhosis. In this assay, a mouse anti-human IgG monoclonal antibody is used to capture all IgG molecules. For both serum samples, samples were pre-cleared with human serum albumin (HSA) or with Galα-1-3Galβ1-(3)4GlcNAc (alpha-gal) linked to HSA. Captured samples were either probed with a secondary mouse anti human IgG antibody (column 1) or with the fucose binding lectin AAL (column 2). As columns 1 & 3 of FIG. 4 show, no significant change in IgG binding was observed from the healthy and cirrhotic patient as a function of blocking agents. Column 2 of FIG. 4 shows the lectin reactivity of the captured IgG molecules. As before, no signal is detected from the healthy samples regardless of pre-treatment. In contrast, strong AAL binding of captured human IgG from patients with cirrhosis was observed when samples were pre-cleared with HSA (column 2). However, when alpha-gal reactive antibodies have removed, even though large amounts of IgG are still captured on the plate (column 3) greatly reduced binding of the lectin is observed (column 4), indicating that alpha-gal antibodies specifically are altered with the development of cirrhosis. Additionally, when the IgG is denatured before analysis in an IgG lectin-FLISA, all patient samples are reactive to the fucose specific lectin, suggesting that the lectin reactivity IgG is conformation dependent.

Example 5: Glycosylation of Human IgG Changes with the Development of Cirrhosis

We performed glycan analysis on anti-gal IgG via N-linked glycan sequencing. Purified anti-gal IgG was isolated from either control patients or patients with HCV induced cirrhosis and 1 μg resolved via SDS-PAGE (FIG. 5A). Subsequently, structural N-linked glycan analysis of the heavy chains was performed and is shown in FIGS. 5B and 5C. Significant differences can be seen on the glycans from patients with cirrhosis as compared to the healthy patients (compare FIG. 5B with 5C). While healthy subjects contained primarily a FcA2G2 glycan structure, the heavy chain from patients with cirrhosis contained truncated structures containing either a single galactose residue (FcA2G1) or no galactose residues (FcA2G0). The agalactosylated core fucosylated biantennary N-glycan (FcA2G0) was also observed in the glycomic analysis of total serum as shown in FIG. 1A. N-linked glycans were not observed on light chains, either via lectin blot or by glycan sequencing. There thus, appears to be a consistent structural difference between the IgG isolated from healthy individuals and those with cirrhosis, and this change (agalactose) has been associated with a pro-inflammatory structure (Kaneko, et al., 2006. Science 313:670-3; Lastra, et al., 1998. Autoimmunity 28:25-30).

Figure 6A:
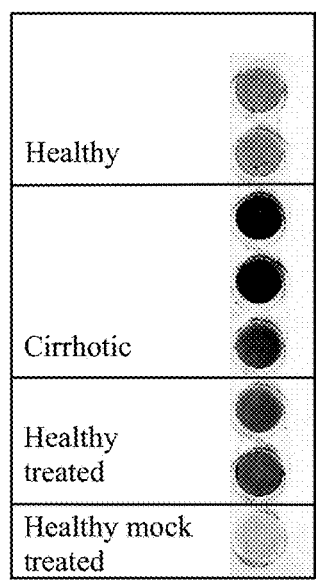
FIGS. 6A-C are respectively a photograph, HPLC graph, and graph depicting the reactivity of human IgG to the fucose binding lectin AAL is dependent by the type of N-linked glycan attached.
Figure 6B:
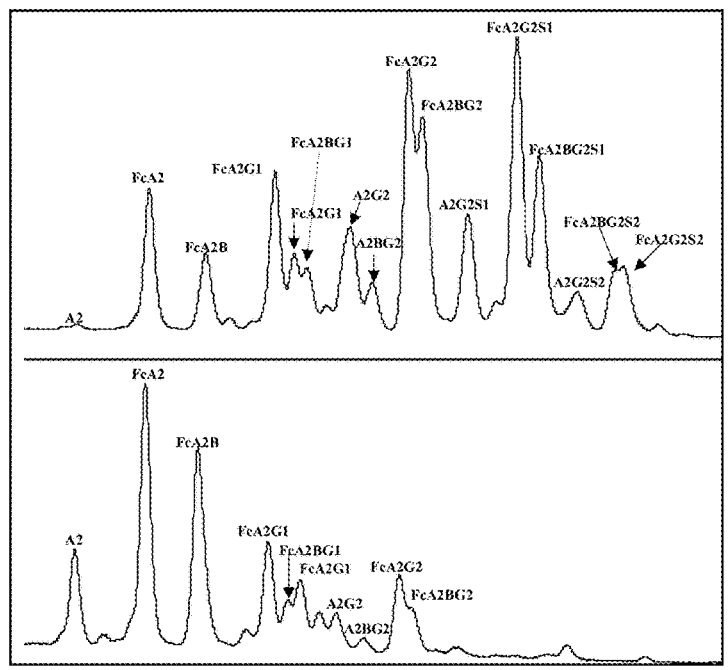
Figure 6C:
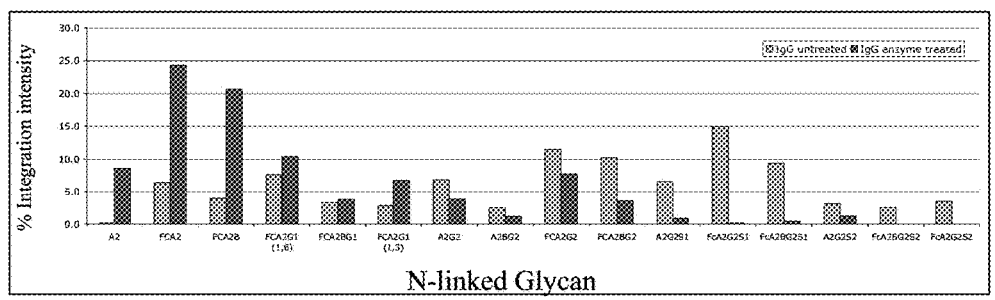

Example 6: The Change in Glycosylation of Human IgG Allows for Interaction with Fucose Binding Lectins The relationship between the change in glycosylation observed in cirrhosis (FIGS. 5B and 5C) and the increased reactivity with fucose binding lectins (FIGS. 1-4) was tested by altering the glycan structure on IgG from healthy individuals to mimic that observed in patients with fibrosis/cirrhosis. This was done by treating purified IgG from healthy individuals, which does not interact with the fucose binding lectin AAL, with sialidase (*Arthrobacter ureafaciens*) and beta-galactosidase (Jack Bean), to create the degalactosylated N-linked glycan normally found on IgG patients with cirrhosis (Nimmerjahn, et al., 2007 Proc Natl Acad Sci USA 104:8433-7). The reactivity of these samples with the fucose binding lectins was tested using a lectin-FLISA for captured IgG. Consistent with the results obtained in FIGS. 2-5, while IgG from control serum is not reactive with fucose binding lectins, IgG from cirrhotic patients is highly reactive (FIG. 6A). Reactivity with fucose binding lectin was obtained when IgG was degalactosylated enzymatically, suggesting that the increased reactivity of IgG to the fucose binding lectins is partially associated with the degalactosylated glycan structure (FIGS. 6A & 6B). Treatment of samples with just sialidase alone had no effect on binding, while treatment with or beta-galactosidase alone had only a minor effect. Glycan sequencing on treated IgG was performed to confirm glycan modification (FIG. 6C). Thus, the increased reactivity of the IgG from cirrhotic individuals with fucose binding lectins is partially related to the truncated glycosylation of the IgG molecule.

Example 7: Increased Reactivity of a Fucose Specific Lectin with Human IgG Appears to Correlate with the Development of Cirrhosis Using the same lectin FLISA shown in FIGS. 2-4, the relative amount of lectin reactive IgG was determined in 257 coded serum samples from either control subjects, those with HCV induced cirrhosis and those with HCV induced cirrhosis plus HCC. The results are shown in FIG. 7A and are expressed as "fold increase" over commercially purchased human serum.

Figure 7A:
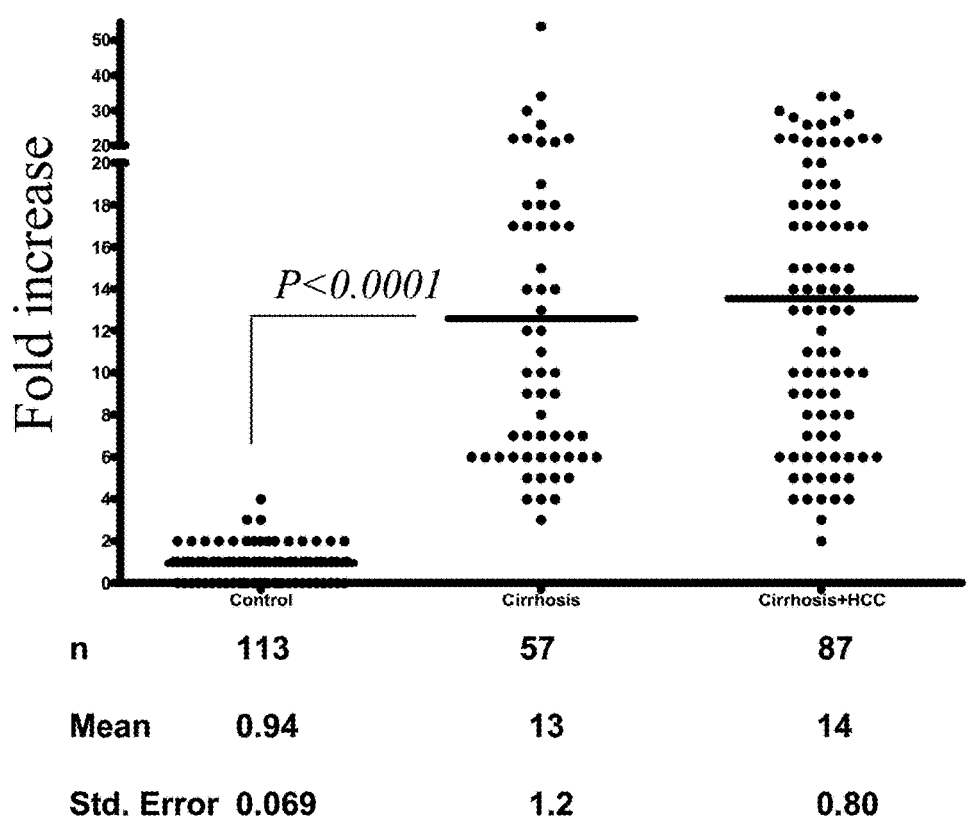
FIGS. 7A-B are graphs quantitating lectin reactive IgG in patients with HCV induced fibrosis and cirrhosis.

The signal detected in the samples from the 113 control subjects was similar to that observed in commercially purchased serum, with a mean relative value of 0.94 (FIG. 7A). In contrast, 57 patients with HCV induced cirrhosis had values greater than 3 fold above commercially purchased serum with a mean increase of 13 fold. This difference was statistically significant (P<0.0001; Two-tailed Mann-Whitney test) confirming our results in FIGS. 2-6.

As the fucosylation of many proteins has been shown to be increased in HCC (Comunale, et al., 2006. J Proteome Research. 6:308-315; Drake, et al., 2006 Mol Cell Proteomics 5:1957-1967), it was of interest to see if greater lectin reactivity would be observed in patients with cirrhosis plus HCC. Therefore the level of lectin reactive IgG was measured in 87 patients with HCV induced cirrhosis plus HCC. As FIG. 7A shows, patients with cirrhosis plus HCC had a mean 14 fold increase in lectin reactive IgG, which was not statistically different than the increase observed in patients with cirrhosis alone. Thus, no further increases in lectin binding could be observed with the development of HCC.

Figure 7B:
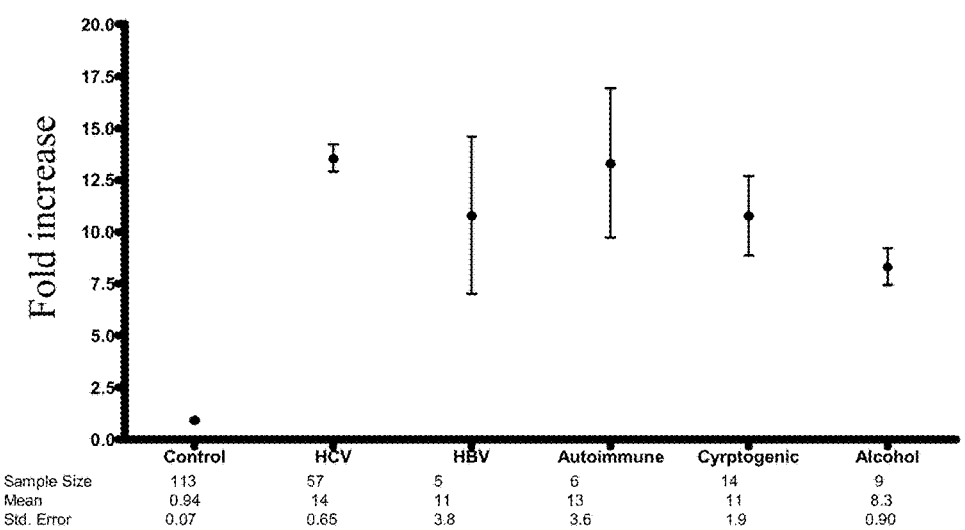

Example 8: Fucose Detection of Anti-Gal IgG is Observed in Patients with Cirrhosis from Multiple Etiologies To determine if the lectin reactivity with IgG was a phenomenon that correlated with the development of cirrhosis, independent of the etiology, we examined the level of lectin reactive IgG in patients with cirrhosis induced from excessive alcohol consumption, autoimmune disease, HBV infection or from patients with an unknown underlying disease. As FIG. 7B shows, although the sample size is limited, the trend is very clear: IgG from patients with cirrhosis, regardless of the underlying etiology, have greater reactivity to fucose specific lectins as compared to healthy controls. Similar to the results obtained in FIGS. 3-5, all patients with cirrhosis had >3 fold elevations in lectin reactive IgG. Statistical difference was observed for all individual cirrhotic groups (from non HCV induced cirrhosis) when compared to control subjects (P<0.0001; Mann Whitney test). However, no statistical difference was observed between individual cirrhotic groups (One-way ANOVA; Kruskal-Wallis test).

Figure 8A:
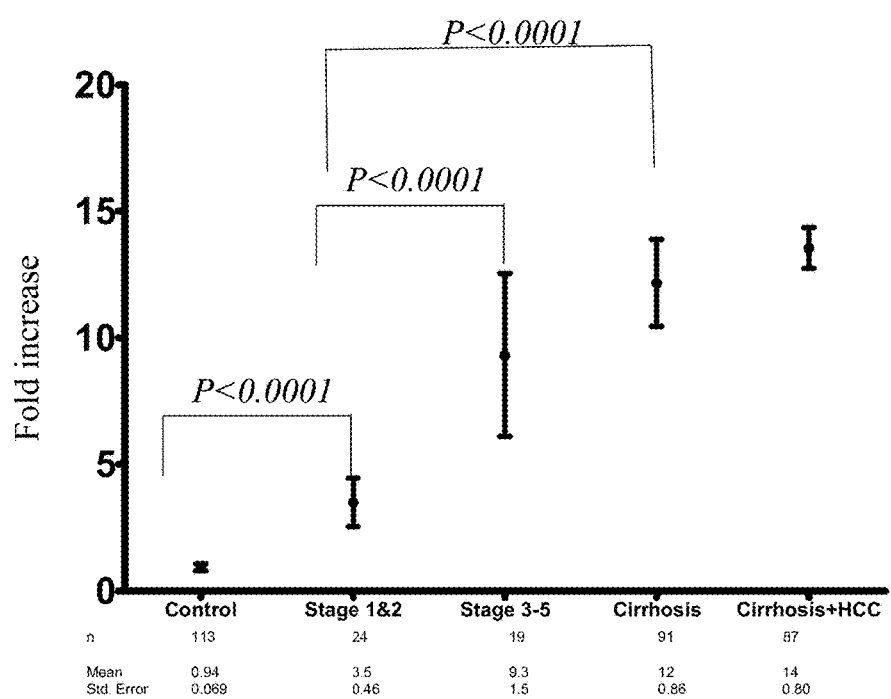
FIGS. 8A-C are graphs depicting the increase in lectin reactive anti-gal IgG with the development of liver fibrosis.

Example 9: Increased Fucose Detection of Anti-Gal IgG is Observed in Patients with Fibrosis As the level of lectin reactive anti-gal IgG was increased in patients with cirrhosis, it was of interest to determine if similar changes could be observed in patients with fibrosis. Thus we examined the level of lectin reactive anti-gal IgG in patients with either limited fibrosis (stage 1-2) or more severe fibrosis (stage 3-4). These data are shown in FIG. 8A along with the data from patients from the control or cirrhosis groups. As this Figure shows, stage 1&2 fibrotic patients had a mean increase of 3.5 fold over commercially purchased sera, compared to only a 0.94 fold increase in the control patients. Even with the small sample size (n=24) this increase was statistically different from the control group (P<0.0001; Two-tailed Mann-Whitney test) implying that the change in IgG starts with the development of liver fibrosis.

Patients with bridging fibrosis and incomplete cirrhosis (stage 3-5) had an even greater level of lectin reactive IgG with a mean increase of 9.3 fold over commercially purchased sera. Although the sample size was limited (n=19), significant statistical difference (P<0.0001; Two-tailed Mann-Whitney test) was observed between those patients with limited fibrosis (stage 1&2) and those with more severe fibrosis (stage 3&5). No statistical difference was observed between patients with bridging fibrosis (Stage 3&5) and those patients with cirrhosis (P>0.5).

Figure 8B:
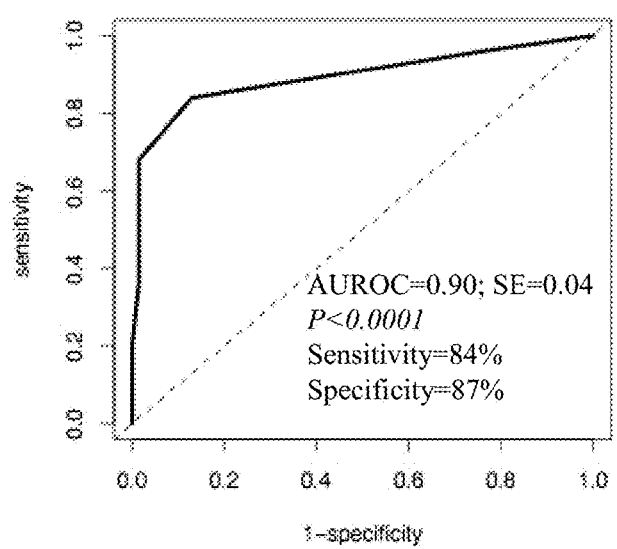
Figure 8C:
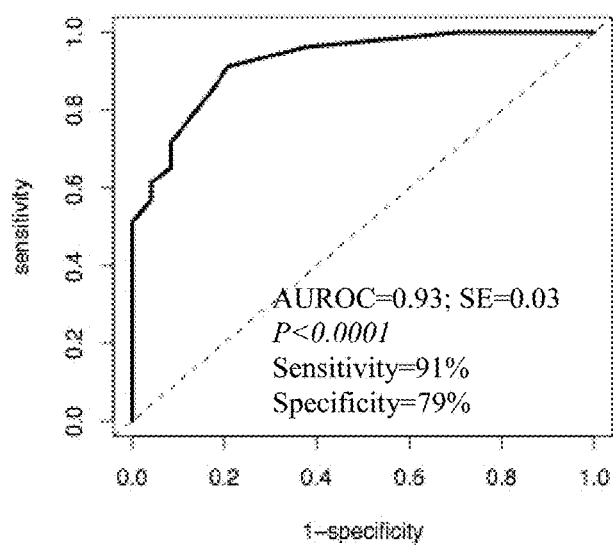

Receiver operator characteristic (ROC) curves were plotted to help define the optimal cutoff values for differentiating the different stages of liver fibrosis and cirrhosis. ROC analysis was performed between stage 1&2 fibrosis and control subjects and between stage 1 & 2 fibrosis and stage 3-6 fibrosis/cirrhosis. FIG. 8B shows the AUROC for the analysis of control subjects versus stage 1&2 fibrosis was 0.90 with significant statistical difference between the observed curve and no-discrimination line (P<0.0001). Using a cutoff of 3 fold above commercially purchased sera, lectin reactive anti-gal IgG had a sensitivity of 84%, a specificity of 87%, a positive predictive value (PPV) of 70% and a negative predictive value (NPV) of 94%. The ROC analysis for the differentiation of those patients with limited fibrosis (stage 1 & 2) and those with stage 3 or greater fibrosis is shown in FIG. 8C. In such an analysis, the AUROC curve for fucosylated IgG was 0.93 with a sensitivity of 91% and a specificity of 79%, using an optimal cutoff of 5 relative units.

What is claimed:

1. A method for assessing the severity of fibrosis in a subject suspected of having fibrosis comprising:
    separating anti-gal IgG from a biological fluid of said subject using a separation agent;
    contacting said separated anti-gal IgG from said biological fluid with a fucose-binding reagent, and allowing said reagent to bind to said anti-gal IgG;
    quantifiably detecting fucose-binding reagent bound to said anti-gal IgG to obtain a detected bound reagent value;
    comparing the detected bound reagent value with a reference value for reagent binding on said anti-gal IgG from a comparable biological fluid of one or more subjects without fibrosis; and,
    staging the severity of fibrosis in said subject as one of no fibrosis, limited fibrosis, or severe fibrosis, based on the results of said comparison.

2. The method according to claim 1 wherein the biological fluid is whole blood, serum, urine, saliva, tears, or mucous.

3. The method according to claim 1 wherein said separation agent comprises lectins, antibodies, or polypeptides by carbohydrate-recognition domains.

4. The method according to claim 1 wherein said fucose-binding reagent is a lectin.

5. The method according to claim 1 wherein the fucose-binding reagent is coupled to a detectable moiety.

6. The method according to claim 1 wherein the severity of fibrosis in said subject is staged as limited when the detected bound reagent value is about three to about five times greater than said reference value for reagent binding.

7. The method according to claim 1 wherein the severity of fibrosis in said subject is staged as severe when the detected bound reagent value is about six to about 13 times greater than said reference value for reagent binding.

8. The method according to claim 1 wherein limited fibrosis corresponds to either of fibrosis stages 1 or 2 according to the Ishak scoring system.

9. The method according to claim 1 wherein severe fibrosis corresponds to any of fibrosis stages 3-5 according to the Ishak scoring system.

10. A method for assessing the severity of fibrosis in a subject suspected of fibrosis comprising:
    quantifiably detecting fucosylated anti-gal IgG from a biological fluid of said subject to provide a detected fucosylated anti-gal IgG value, wherein said detecting step utilizes an assay comprising a fucose-binding reagent,
    wherein a comparison of the detected fucosylated anti-gal IgG value to a reference value for fucosylated anti-gal IgG from a comparable biological fluid of one or more persons without fibrosis is determinative of whether said subject has no fibrosis, limited fibrosis, or severe fibrosis.

11. The method according to claim 10 further comprising utilizing a separation agent to separate said fucosylated IgG from the biological fluid prior to quantifiably detecting the fucosylated anti-gal IgG.

12. The method according to claim 11, wherein said separation agent comprises lectins, antibodies, or polypeptides by carbohydrate-recognition domains.

13. The method according to claim 10 wherein said fucose-binding reagent is a lectin.

14. The method according to claim 10 wherein said limited fibrosis corresponds to either of fibrosis stages 1 or 2 according to the Ishak scoring system.

15. The method according to claim 10 wherein said severe fibrosis corresponds to any of fibrosis stages 3-5 according to the Ishak scoring system.

16. The method according to claim 10 wherein a detected fucosylated anti-gal IgG value that is about three times to about five times a reference value for fucosylated anti-gal IgG from a comparable biological fluid of one or more subjects without fibrosis is indicative of the presence of limited fibrosis.

17. The method according to claim 10, wherein a detected fucosylated anti-gal IgG value that is about six times to about 13 times a reference value for fucosylated anti-gal IgG from a comparable biological fluid of one or more subjects without fibrosis is indicative of the presence of severe fibrosis.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Homo sapiens

<400> SEQUENCE: 1

```
Glu Glu Gln Tyr Asn Ser Thr Tyr Arg
1               5

<210> SEQ ID NO 2
<211> LENGTH: 19
<212> TYPE: PRT
<213> ORGANISM: Homo sapiens

<400> SEQUENCE: 2

Glu Val Gln Leu Val Glu Ser Gly Gly Gly Leu Val Lys Pro Gly Gly
1               5                   10                  15

Ser Leu Arg

<210> SEQ ID NO 3
<211> LENGTH: 11
<212> TYPE: PRT
<213> ORGANISM: Homo sapiens

<400> SEQUENCE: 3

Asn Thr Leu Tyr Leu Gln Met Asn Ser Leu Lys
1               5                   10
```